US008864741B2

(12) United States Patent
Lilley

(10) Patent No.: US 8,864,741 B2
(45) Date of Patent: Oct. 21, 2014

(54) VARICOSE VEIN TREATMENT

(75) Inventor: Jean-Pierre Lilley, Edgbaston (GB)

(73) Assignee: Jean-Pierre Lilley, Edgbaston, Birmingham ( * ) Notice: Subject to any disclaimer, the term of this patent is extended or adjusted under 35 U.S.C. 154(b) by 0 days.

(21) Appl. No.: 12/993,797

(22) PCT Filed: May 19, 2009

(86) PCT No.: PCT/GB2009/001236
§ 371 (c)(1),
(2), (4) Date: Nov. 19, 2010

(87) PCT Pub. No.: WO2009/141591
PCT Pub. Date: Nov. 26, 2009

(65) Prior Publication Data
US 2011/0060277 A1    Mar. 10, 2011

Related U.S. Application Data

(60) Provisional application No. 61/054,276, filed on May 19, 2008.

(51) Int. Cl.
| | | |
|---|---|---|
| A61M 31/00 | (2006.01) | |
| A61B 17/00 | (2006.01) | |
| A61B 19/02 | (2006.01) | |
| A61B 17/135 | (2006.01) | |
| A61B 19/04 | (2006.01) | |
| A61B 17/132 | (2006.01) | |

(52) U.S. Cl.
CPC ......... *A61B 17/00491* (2013.01); *A61B 19/026* (2013.01); *A61B 17/135* (2013.01); *A61B 19/04* (2013.01); *A61B 17/132* (2013.01); *A61B 17/00008* (2013.01)

USPC ........................................................ 604/508

(58) Field of Classification Search
USPC ......... 604/181, 187, 207, 218, 507, 508, 509;
602/13, 75; 606/201–203
See application file for complete search history.

(56) References Cited

U.S. PATENT DOCUMENTS

| | | | | |
|---|---|---|---|---|
| 4,316,461 A | * | 2/1982 | Marais et al. | ................. 604/179 |
| 4,597,384 A | | 7/1986 | Whitney | |

(Continued)

FOREIGN PATENT DOCUMENTS

| | | |
|---|---|---|
| CN | 1403164 A | 3/2003 |
| CN | 1418706 A | 5/2003 |

(Continued)

OTHER PUBLICATIONS

"Sclerotherapy for Varicose Veins", Web accessed Feb. 13, 2008; http://health.yahoo.com.

(Continued)

*Primary Examiner* — Aarti B Berdichevsky
(74) *Attorney, Agent, or Firm* — Arent Fox LLP

(57) ABSTRACT

Methods for treating an undesired varicose or spider vein in a venous system of a patient generally includes substantially emptying the vein of blood between its proximal end and distal end; introducing a medically acceptable adhesive into the substantially emptied vein; and applying pressure to the vein to cause the opposing side walls of the vein to be adhered together in a collapsed configuration by the adhesive. Also disclosed are kits for the treatment of undesired varicose or spider vein in a venous system of a patient. The kits include a medically acceptable adhesive; a cannula; a guide wire; and a catheter.

8 Claims, 2 Drawing Sheets

(56) References Cited

U.S. PATENT DOCUMENTS

| | | | |
|---|---|---|---|
| 4,834,802 A * | 5/1989 | Prier | 606/203 |
| 4,870,978 A * | 10/1989 | Atwell | 128/898 |
| 5,022,399 A | 6/1991 | Biegeleisen | |
| 5,478,119 A | 12/1995 | Dye | |
| 5,624,669 A | 4/1997 | Leung et al. | |
| 5,626,556 A | 5/1997 | Tobler et al. | |
| 5,626,557 A * | 5/1997 | Mann | 602/26 |
| 5,693,068 A * | 12/1997 | Kuhlman | 606/201 |
| 5,695,520 A * | 12/1997 | Bruckner et al. | 606/204 |
| 5,795,312 A | 8/1998 | Dye | |
| 5,865,779 A * | 2/1999 | Gleason | 602/30 |
| 6,007,544 A | 12/1999 | Kim | |
| 6,224,622 B1 | 5/2001 | Kotzev | |
| 6,231,532 B1 | 5/2001 | Watson et al. | |
| 6,652,559 B1 | 11/2003 | Tetreault et al. | |
| 6,719,711 B1 * | 4/2004 | Islava | 602/13 |
| 2003/0044219 A1 | 3/2003 | Quintero | |
| 2003/0045860 A1 | 3/2003 | Leu | |
| 2003/0194389 A1 | 10/2003 | Porter | |
| 2003/0194390 A1 * | 10/2003 | Krall et al. | 424/78.35 |
| 2004/0092913 A1 | 5/2004 | Hennings et al. | |
| 2004/0254589 A1 | 12/2004 | Darnis et al. | |
| 2005/0065531 A1 | 3/2005 | Cohen | |
| 2005/0107738 A1 * | 5/2005 | Slater et al. | 604/96.01 |
| 2005/0107867 A1 | 5/2005 | Taheri | |
| 2005/0113858 A1 * | 5/2005 | Deutsch | 606/195 |
| 2005/0153090 A1 | 7/2005 | Marchitto et al. | |
| 2005/0182443 A1 | 8/2005 | Jonn et al. | |
| 2005/0187501 A1 | 8/2005 | Ravikumar | |
| 2005/0187503 A1 * | 8/2005 | Tordella et al. | 602/13 |
| 2005/0267570 A1 | 12/2005 | Shadduck | |
| 2006/0009099 A1 | 1/2006 | Jonn et al. | |
| 2006/0052823 A1 * | 3/2006 | Mirizzi et al. | 606/214 |
| 2006/0079824 A1 | 4/2006 | Munch-Fals et al. | |
| 2006/0106350 A1 | 5/2006 | Spitz | |
| 2006/0149218 A1 | 7/2006 | Slater et al. | |
| 2006/0149309 A1 | 7/2006 | Paul et al. | |
| 2006/0161197 A1 | 7/2006 | Paul et al. | |
| 2006/0211987 A1 * | 9/2006 | Williams | 604/116 |
| 2006/0251612 A1 | 11/2006 | Kotzev et al. | |
| 2007/0129658 A1 * | 6/2007 | Hampson et al. | 602/13 |
| 2007/0166345 A1 | 7/2007 | Pavcnik et al. | |
| 2007/0191825 A1 | 8/2007 | Cronin et al. | |
| 2007/0248640 A1 | 10/2007 | Karabey et al. | |
| 2007/0292472 A1 * | 12/2007 | Paul et al. | 424/423 |
| 2008/0249447 A1 * | 10/2008 | Brown et al. | 602/13 |
| 2009/0257976 A1 | 10/2009 | Kerber et al. | |
| 2010/0217306 A1 | 8/2010 | Raabe et al. | |
| 2010/0217313 A1 | 8/2010 | Raabe et al. | |

FOREIGN PATENT DOCUMENTS

| | | |
|---|---|---|
| CN | 1660068 A | 8/2005 |
| CN | 1692951 A | 11/2005 |
| DE | 42 30 165 A1 | 3/1994 |
| EP | 0 552 515 A1 | 7/1993 |
| LV | 12856 B | 11/2002 |
| WO | WO 96/23532 A1 | 8/1996 |
| WO | WO 00/44287 A1 | 8/2000 |
| WO | WO 01/89501 A1 | 11/2001 |
| WO | WO 02/00097 A2 | 1/2002 |
| WO | WO 2006/053920 A2 | 5/2006 |
| WO | WO 2006/134354 A1 | 12/2006 |
| WO | WO 2007/030892 A1 | 3/2007 |

OTHER PUBLICATIONS

"Tissue Adhesives: Histoacryl®—The Real Thing", Web accessed Feb. 14, 2008; http://www.bbraun.com.

* cited by examiner

VARICOSE VEIN TREATMENT

CROSS-REFERENCE TO RELATED APPLICATION

This application is a National Stage entry of International Application No. PCT/GB2009/001236, filed May 19, 2009, which claims priority to U.S. Provisional Application No. 61/054,276, filed May 19, 2008. The disclosures of the prior applications are hereby incorporated in their entirety by reference.

BACKGROUND

This invention relates generally to surgical apparatus and procedures. More particularly, it relates to methods and apparatus for treatment of unwanted varicose, reticular and spider veins in a venous system of a patient.

Spider veins, reticular veins and varicose veins are common conditions that occur in many humans and are typically found in the limbs of the human body, in particular the legs.

Spider veins (i.e., telangiectasiae) are small, dilated blood vessels near the surface of the skin. They can develop anywhere on the body but commonly are found on the face, around the nose, cheeks, and chin, or on the legs, in particular on the upper thigh, below the knee joint, and around the ankles. Reticular veins are also known as feeder veins and are dilated veins that appear bluish or greenish in colour and are visible to the naked eye. Spider and reticular veins generally consist of small, thin, dark-colour veins that lie close to the surface of the skin. Usually they measure only a few millimeters. They often have a web or sunburst pattern, but may also appear as random line segments.

Varicose veins are larger than spider veins. Varicose veins are bulging veins that are typically 3 millimeters (mm) or more in diameter. They generally are veins that have become enlarged and twisted. Varicose veins are most commonly found on the leg, although varicose veins can occur elsewhere on the body. Varicose veins usually have a blue or purple colour and may protrude above the surface of the skin. These veins have usually lost their ability to carry blood back to the heart and blood often accumulates in these veins.

A number of factors can contribute to the development of varicose and spider veins, including heredity, obesity, posture, hormonal shifts, excessive heat, and standing or sitting for a long periods of time.

Reticular and varicose veins may cause patients to experience symptoms such as aching, burning, swelling, cramping, and itching. More serious complications of varicose veins can include thrombophlebitis, dermatitis, haemorrhage, and ulcers.

If certain varicose veins are not treated, blood clots may form in the vein, and phlebitis or inflammation of the inside lining of the vein may occur.

Equally, many patients seek medical treatment of varicose veins and spider veins for cosmetic reasons.

Various approaches have been developed to treat spider, reticular and varicose veins. These treatments include vein removal for severe cases; for example, using techniques such as ambulatory phlebotomy or vein stripping. Such operations can be painful and uncomfortable for patients in the hours and days following surgery.

Endovenous laser and radiofrequency ablation are also known methods of treatment. However, these methods require specialized training for practitioners and expensive equipment. Follow-up treatment for smaller branch varicose veins is also often needed in the weeks after the initial procedure. Complications for radiofrequency ablation and endovenous laser treatment include bruising, burns and paraesthesia.

In less complicated cases, elevation of the legs and use of support hosiery may be sufficient therapy to stop or slow the progression of the varicose veins.

Sclerotherapy is a well known treatment for smaller varicose and spider veins lying close to the surface of the skin. In this procedure, the affected veins are injected with a sclerosing solution, such as sodium tetradecyl sulfate (STS). The sclerosing solution causes inflammation and subsequent sclerosis of the vein. The sclerosis results in localized scarring of the veins, which forces re-routing of the blood away from the affected veins.

When treating veins with a sclerosing solution, the sclerosing solution may not stay in the desired portion of the vein being treated and may leak outside of the vein, causing skin ulcerations. Hyper-pigmentation may also occur as a result of the leakage of a blood component, hemosiderin pigment, from the treated vein. The sclerosing solution can also cause inflammation in the region where the solution was injected.

In order to limit postoperative inflammation, the medical practitioner usually applies compression to the treated area immediately after sclerosing solution has been injected. The patient is also usually required to wear support hosiery for a number of days, e.g., for 48 consecutive hours after treatment and then during waking hours for seven more days.

SUMMARY OF THE INVENTION

In view of the above, the present invention provides methods and apparatus for treating undesired veins, specifically varicose, spider and reticular veins, in a venous system of a patient.

In a first aspect, the present invention provides a method of treating an undesired varicose, reticular or spider vein in a venous system of a patient, the undesired vein having opposing side walls and extending from a proximal end to a distal end, the method comprising the steps of substantially emptying the vein of blood between its proximal end and distal end; introducing an adhesive into the substantially emptied vein; and applying pressure to the vein to cause the opposing side walls of the vein to be adhered together in a collapsed configuration by the adhesive.

The undesired vein may be in any part of the patient's body; typically it will be in the patient's leg. In one embodiment, the vein is in the leg and below the knee.

The vein may be substantially emptied of blood by any known method of exsanguination. For example, this may be by raising the part of the patient's body within which the vein is located. In particular, the vein may be located in the patient's leg and the vein is substantially emptied of blood by raising the patient's leg. Alternatively, compression techniques/devices may be used to exsanguinate. This may include manual application of pressure along the vein to empty blood from the vein.

For example, if there are no tributaries in the length of vein to be treated, the vein may be substantially emptied of blood by maintaining pressure on the vein and both its ends.

A compression bandage may also be used to exsanguinate through compression. A tensor bandage (e.g. an Ace® wrap bandage) or other elastic bandage may be used. For example, a rubber bandage, e.g. of the Esmarch type, may be used to exsanguinate. Such bandages, which are typically 5 to 10 centimeters (cm) wide, are wrapped in a spiral around the part of the patient's body within which the vein is located to squeeze out the blood.

In one embodiment, after the vein has been substantially emptied of blood, pressure is then applied in order to prevent the vein re-filling with blood. Pressure may in particular be applied to one or both the proximal end and distal end of the vein. The pressure is applied after substantially emptying the vein of blood and before the step of introducing an adhesive into the substantially emptied vein. Preferably, it is maintained during the step of introducing the adhesive into the substantially emptied vein. It may be maintained during the step of applying pressure to the vein to cause the opposing side walls of the vein to be adhered together in a collapsed configuration by the adhesive.

In one such embodiment, a tourniquet is applied to prevent the vein re-filling with blood.

The adhesive may be introduced into the vein using a catheter, such as a venous catheter. Preferably, adhesive is injected into the vein using a catheter.

The catheter should be flexible, for example it may be made of a flexible plastics or rubber material, such as polyurethane, polyethylene, polypropylene, poly vinyl chloride, fluorinated ethylene propylene polymer or latex rubber. Silicone materials may also be used. A coating, such as a silicon elastomer coating or a hydrophilic polymer coating, may be used as required. For example, PTFE coated latex may be used.

Clearly, the interior of the catheter that will contain the adhesive should be made of a material that is compatible with the adhesive; in particular material that does not react with and is not corroded by the adhesive.

The catheter may be any suitable length. In the event that a long vein is treated, more than one catheter may be used, for example two catheters may be used.

The length of catheter will be partly determined by whether the catheter is to be inserted along the entire length of the unwanted vein in order to directly inject the adhesive along the length of the vein or whether the catheter is to be used to simply inject the adhesive at one end of the vein with pressure then being used to force the adhesive along the length of the vein.

In the former situation, the catheter should be as long as, or longer than, the unwanted vein to be treated. The length of a varicose vein can be from, for example, 2 cm to 60 cm, commonly from 5 cm to 50 cm, such as from 5 cm to 25 cm.

In one embodiment, the catheter has a length of 25 cm or less, e.g. from 5 cm to 20 cm, such as from 10 cm to 15 cm. In one embodiment, the catheter has a length of from 10 cm to 20 cm. In the event that a long vein is treated, more than one catheter may be used, for example two catheters may be used.

The catheter should be sized in terms of its diameter to be introduced into the unwanted vein. Varicose veins may typically have a diameter of 3 mm or greater, e.g. from 4 mm to 15 mm. Spider and reticular veins typically have a smaller diameter, such as 3 mm or less, e.g. from 0.5 mm to 2 mm.

For example, the catheter may be 16 to 22 gauge, such as 17 to 21 gauge. In one embodiment, the catheter is 18-gauge, 19-gauge or 20-gauge.

In a first embodiment, the catheter is introduced into the vein, along its length, such that a distal end of the catheter is located at or near the distal end of the vein. The catheter is then withdrawn from the distal end of the vein towards the proximal end of the vein, with adhesive being introduced into the vein from the distal end of the catheter as the catheter is withdrawn.

Preferably, in such an embodiment, the catheter is introduced into the vein using a guide wire as a placement guide. Specifically, a guide wire may be located in the unwanted vein, and the catheter passed over this guide wire to ensure correct location of the catheter in the vein. The guide wire may then be withdrawn. In such an embodiment, the catheter suitably has a distal lumen to run over the wire.

The guide wire may be any suitable wire. In one embodiment, it may be a flexible guide wire. Suitably, it may have a J shaped tip. The guide wire may be any suitable length. The guide wire should, however, preferably be longer than the catheter, e.g. at least 1 cm longer than the catheter, such as at least 5 cm longer than the catheter, e.g. at least 10 cm longer than the catheter. In one embodiment, the guide wire has a length of 10 cm or greater, such as 15 cm or greater, e.g. 20 cm or greater.

More preferably, in this embodiment, the catheter is introduced into the vein using a Seldinger wire technique. As the skilled man will appreciate, this is a method of percutaneous insertion of a catheter into a blood vessel, whereby a needle or other sharp ended instrument is used to puncture the vessel and a guide wire is threaded through the needle; when the needle is withdrawn, a catheter is threaded over the wire; the wire is then withdrawn, leaving the catheter in place.

In particular, in the present invention the guide wire may be introduced into the vein using a sharp ended cannula, e.g. a cannula provided with a trocar. In particular, a cannula with an integral trocar may be used. The cannula is used to puncture the unwanted vein. The guide wire is then introduced into the cannula and threaded along the vein. Preferably, the guide wire is threaded along the maximum length of vein that can be navigated.

The guide wire may be threaded along the vein under direct vision of the unwanted vein. Alternatively, an imaging tool, e.g. ultrasound or radiography, can be used to visualise the unwanted vein. In one embodiment, ultrasound is used.

In a second embodiment, the end of the catheter is introduced into the vein at or near one end, following the use of a cannula to puncture the unwanted vein at the required location. The catheter is then used to inject the adhesive at this one end of the vein. External pressure is then applied to force the adhesive along the length of the unwanted vein.

This second embodiment is generally more appropriate for small unwanted veins, which are delicate and could be broken by attempting to pass a catheter along their length, whereas the first embodiment involving insertion of the catheter along the entire vein length is more appropriate for large unwanted veins, where the injection of adhesive as the catheter is drawn back along the length of the vein will ensure sufficient adhesive is applied along the length of the large vein.

In any embodiments, the cannula should be of a suitable size for cannulating the vein. The cannula is suitably an intravenous cannula.

The cannula may, for example, be a 20 to 26 gauge cannula, such as a 22-gauge or 24-gauge cannula.

The cannula should be introduced into the vein before the vein has been substantially emptied of blood. The vein should be full or substantially full to cannulate. Therefore, in a preferred embodiment, the cannula is introduced into the vein before the step of substantially emptying the vein of blood is started.

In a preferred embodiment, the method further comprises a step of substantially emptying of blood at least one blood vessel that connects with the undesired vein, prior to the step of introducing the adhesive. It is preferred that the method comprises a step of substantially emptying of blood each blood vessel that connects with the undesired vein, prior to the step of introducing the adhesive. This may entail flushing the vein with glucose solution.

Most preferably, the method comprises a step of substantially emptying of blood each blood vessel within a vicinity of at least 1 cm of the undesired vein of blood, prior to the step of introducing the adhesive. It is most preferred that the method comprises a step of substantially emptying of blood each blood vessel within a vicinity of at least 2 cm, e.g. 3 cm, 4 cm or 5 cm, of the undesired vein of blood, prior to the step of introducing the adhesive. This may entail flushing the vein with glucose solution.

It is advantageous to ensure that blood is emptied from blood vessels connecting with/in the vicinity of the undesired vein prior to introducing the adhesive. The present inventor has identified that this step will ensure that the adhesive does not enter into surrounding blood vessels, as there is no blood flow to allow the adhesive to enter into these blood vessels, and therefore avoids any potential problems caused by entry of the adhesive into major blood vessels, such as an embolism.

In a preferred embodiment, blood is emptied from blood vessels connecting with/in the vicinity of the undesired vein prior to the step of substantially emptying the undesired vein of blood. In another embodiment, blood is emptied from blood vessels connecting with/in the vicinity of the undesired vein after to the step of substantially emptying the undesired vein of blood.

Blood may be emptied from blood vessels connecting with/in the vicinity of the undesired vein using compression. In a preferred embodiment, blood is emptied from blood vessels connecting with/in the vicinity of the undesired vein using a tourniquet or an inflatable cuff. The tourniquet or inflatable cuff is placed over the part of the body containing the blood vessels connecting with/in the vicinity of the undesired vein and is inflated to apply pressure to the blood vessels, in order to expel blood from the blood vessels.

In a first preferred embodiment, blood is emptied from blood vessels connecting with/in the vicinity of the undesired vein using an inflatable cuff that includes a non-inflatable section for location over the undesired vein. This non-inflatable section allows access to the undesired vein, for introduction of the adhesive.

This preferred embodiment is particularly preferred for the treatment of small unwanted veins. For such small veins, the blood in the undesired vein can readily be expelled by manually applying pressure along the undesired end from one end to the other. For such small veins the catheter may be used to simply inject adhesive at one end of the vein and pressure can then be applied so that the adhesive can then move along down the length of the vein; therefore it is important the skin above the undesired vein remains accessible for this injection of adhesive.

Preferably the non-inflatable section is sized so as to cover the undesired vein but so as to substantially not cover any major blood vessels connecting with/in the vicinity of the undesired vein. Most preferably the non-inflatable section is sized so as to cover the undesired vein but so as to substantially not cover any blood vessels connecting with/in the vicinity of the undesired vein.

In one embodiment, the non-inflatable section is from 1 cm to 15 cm (e.g. from 2 cm to 10 cm) in length and from 0.5 cm to 5 cm (e.g. from 1 cm to 3 cm) in width.

In another, related, embodiment, blood is emptied from blood vessels connecting with/in the vicinity of the undesired vein using a tourniquet that includes a cut-out window section for location over the undesired vein. This window section allows access to the undesired vein, for introduction of the adhesive.

Preferably the window section is sized so as to cover the undesired vein but so as to substantially not cover any major blood vessels connecting with/in the vicinity of the undesired vein. Most preferably the window section is sized so as to cover the undesired vein but so as to substantially not cover any blood vessels connecting with/in the vicinity of the undesired vein.

In one embodiment, the window section is from 1 cm to 15 cm (e.g. from 2 cm to 10 cm) in length and from 0.5 cm to 5 cm (e.g. from 1 cm to 3 cm) in width.

The use of an inflatable cuff with a non inflatable section or a tourniquet with a window section allows blood to be expelled from blood vessels connecting with/in the vicinity of the undesired vein without restricting access to the undesired vein. Once the blood has been substantially expelled from blood vessels connecting with/in the vicinity of the undesired vein using the inflatable cuff or tourniquet, the blood in the undesired vein can be expelled, e.g. by manually applying pressure along the undesired end from one end to the other. Alternatively, the blood in the undesired vein can be expelled, e.g. by manually applying pressure along the undesired end from one end to the other and optionally flushing with glucose, prior to expelling blood from blood vessels connecting with/in the vicinity of the undesired vein using the inflatable cuff.

The skin over the undesired vein is left accessible such that the adhesive can be inserted into the vein, e.g. using a catheter.

In a preferred embodiment an inflatable cuff is used and the non-inflatable section of the cuff is a cut-out window section in the cuff which therefore allows direct access to the skin over the undesired vein. Alternatively, the non-inflatable section of the cuff may be made from material that can readily be punctured by a sharp instrument without affecting the ability of the remainder of the cuff to inflate and apply compression to blood vessels.

In a second preferred embodiment, blood is emptied from blood vessels connecting with/in the vicinity of the undesired vein using an inflatable cuff that includes a ridged section for location over the undesired vein. This ridged section applies pressure to the undesired vein, for exsanguination of the vein.

This second preferred embodiment is particularly preferred for the treatment of large unwanted veins. For such large veins, the blood in the undesired vein can be expelled by the application of additional pressure from the ridged section. For such large veins the catheter should be inserted along the length of the vein and this would be done prior to exsanguination. Therefore there is no need to access the skin above the undesired vein once the inflatable cuff has been applied but rather it is important that sufficient pressure is applied to the large undesired vein to empty it of blood before the adhesive is injected using the catheter.

Preferably the ridged section is sized so as to cover the undesired vein but so as to substantially not cover any major blood vessels connecting with/in the vicinity of the undesired vein. Most preferably the ridged section is sized so as to cover the undesired vein but so as to substantially not cover any blood vessels connecting with/in the vicinity of the undesired vein.

In one embodiment, the ridged section is from 0.5 cm to 15 cm (e.g. from 1 cm to 10 cm) in length and from 0.25 cm to 3 cm (e.g. from 0.5 cm to 2 cm) in width.

The ridged section may be any elongate shape but in one embodiment it has a trapezoid or triangular shaped cross section. It is preferred that the shape is one that is wider at its base, which is where it connects with the interior surface of the inflatable cuff, than at its top, which is where, in use, it contacts (directly or indirectly) the skin above the undesired vein. This allows an increased amount of pressure to be applied to the undesired vein to achieve successful exsanguination.

In another, related, embodiment, blood is emptied from blood vessels connecting with/in the vicinity of the undesired vein using a tourniquet that includes a ridged section for location over the undesired vein. This ridged section allows access to the undesired vein, for introduction of the adhesive.

Preferably the ridged section is sized so as to cover the undesired vein but so as to substantially not cover any major blood vessels connecting with/in the vicinity of the undesired vein. Most preferably the ridged section is sized so as to cover the undesired vein but so as to substantially not cover any blood vessels connecting with/in the vicinity of the undesired vein.

In one embodiment, the ridged section is from 0.5 cm to 15 cm (e.g. from 1 cm to 10 cm) in length and from 0.25 cm to 3 cm (e.g. from 0.5 cm to 2 cm) in width.

The use of an inflatable cuff or tourniquet with a ridged section allows blood to be expelled from blood vessels connecting with/in the vicinity of the undesired vein and also from the large undesired vein. Blood can be substantially expelled from blood vessels connecting with/in the vicinity of the undesired vein using the inflatable cuff or tourniquet, and the blood in the large undesired vein can be expelled using the extra pressure from the ridged section. Manually applied pressure along the ridge may be used to assist with exsanguination.

In any of the embodiments that use an inflatable cuff, the inflatable cuff may be secured round a limb containing the undesired vein using releasable securers, such as: hook and loop fastenings, e.g. of the Velcro® type; buttons and corresponding buttonholes; press fit fasteners; tie fasteners; or zip fasteners. The use of such securers allows the inflatable cuff to be firmly secured around the part of the limb containing the undesired vein, e.g. the lower leg, of the patient.

In any of the embodiments that use a tourniquet, the tourniquet may be applied around a limb in a conventional manner, with the tourniquet being applied sufficiently tightly around the limb to exsanguinate.

The tourniquet or inflatable cuff may in one embodiment be sized to fit around an adult calf or around an adult thigh.

The inflatable cuff may include one or more inflatable pouches that can be inflated to apply pressure and cause exsanguination. For example, the inflatable cuff may have one, two, three or four, or more, inflatable pouches. When there is more than one pouch, each pouch may be individually inflated or they may all be inflated simultaneously.

Inflatable cuffs are known, e.g. in sphygmomanometers for measuring blood pressure. The skilled man will therefore be aware of suitable manual and automatic pump options available for causing the inflation and deflation of the inflatable pouches.

A key aspect of the use of the tourniquet or inflatable cuff in the present invention is the controlled exsanguination of blood vessels connecting with/in the vicinity of the undesired vein in order to avoid adhesive travelling into the main blood vessels of the patient, whilst maintaining access to the undesired vein such that the adhesive can be introduced into the undesired vein.

The medically acceptable adhesive used in the invention may be any product that has adhesive properties and is sufficiently non toxic that it can be used in the human body.

The adhesive may, for example, be selected from cyanoacrylate adhesives, fibrin-based adhesives, and polymeric adhesives, e.g. hydrogel polymeric adhesives.

In one preferred embodiment, the medically acceptable adhesive is a cyanoacrylate adhesive. The cyanoacrylate may be any cyanoacrylate that has adhesive properties and is sufficiently non toxic that it can be used in the human body.

The cyanoacrylate may be a product as described in any one of: U.S. Pat. No. 5,624,669, U.S. Pat. No. 3,995,641, U.S. Pat. No. 3,722,599, U.S. Pat. No. 3,559,652, U.S. Pat. No. 3,564,078 and U.S. Pat. No. 3,527,841, the contents of each of which are incorporated herein by reference.

Preferably, the cyanoacrylate is an α-cyanoacrylate of formula:

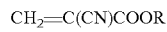

$$CH_2=C(CN)COOR$$

wherein R is an organic group having up to 40 carbon atoms, preferably up to 20 carbon atoms.

Preferably, R is selected from straight chain or branched chain alkyl groups, optionally substituted with one or more group; straight chain or branched chain alkenyl groups; straight chain or branched chain alkynyl groups; cycloalkyl groups; arylalkyl groups; alkoxyalkyl groups; acyloxyalkyl groups; haloalkyl groups; alkylaryl groups; and aryl groups.

When the R group is a substituted alkyl, the substituent groups are suitably selected from an acyloxy group, a halo group; a haloalkyl group, an alkoxy group, a cyano group and a carboxy group. When there is more than one substituent, each may be the same or different.

In one embodiment, R is $CR'_2COOR''$, wherein each R' is hydrogen or methyl and R'' is an organic group, which may be branched or straight chain, such as an alkyl, aryl, aralkyl, alkenyl or alkynyl group, and halo substituted derivatives thereof. Preferably the R'' group has 8 or fewer carbon atoms. In one embodiment, each R' is H, and R'' is a C4-6 alkyl group.

In one embodiment, R is $CHR'CF_2R''$, wherein each R' is hydrogen or methyl or ethyl, and R'' is fluorine, $-CF_3$ or $-(CF_2)_nH$, wherein n is an integer from 1 to 3.

In one embodiment, the alkyl groups have from 1 to 20 carbon atoms, such as from 1 to 16 carbon atoms. In one embodiment, the alkenyl groups have from 2 to 20, e.g. from 2 to 16, carbon atoms. In one embodiment, the alkynyl groups have from 2 to 16, e.g. from 2 to 12, carbon atoms.

Preferably, the cyanoacrylate is an alkyl α-cyanoacrylate, e.g. a C1-C20 α-cyanoacrylate, such as a C1-C12 α-cyanoacrylate, in particular a C1-C8 α-cyanoacrylate. The alkyl group may be straight chain or branched.

In one embodiment, the cyanoacrylate may be C1, C2, C3, C4, C5, C6, C7 or C8 α-cyanoacrylate.

In one embodiment, the cyanoacrylate is methyl 2-cyanoacrylate, n-butyl-2-cyanoacrylate, i-butyl-2-cyanoacrylate, 2-hexyl cyanoacrylate or 2-octyl cyanoacrylate.

The medically acceptable adhesive, e.g. cyanoacrylate, may be used together with one or more medically acceptable carrier, diluent, or excipient.

The medically acceptable adhesive, e.g. cyanoacrylate, may be used together with one or more medically acceptable active ingredient such as a viscosity modifier, e.g. poly(ethyl 2-cyanoacrylate) or poly(lactic acid); or an inhibitor (which may be an acidic stabiliser or a free radical scavenger) e.g. hydroquinone, p-methylphenol or phosphoric acid.

In a preferred embodiment, the medically acceptable adhesive, e.g. cyanoacrylate, may be used together with a retarding agent that slows the rate of curing of the adhesive. This provides more time to carry out the procedure before the adhesive hardens in the vein. In particular, the use of a retarding agent can ensure that the adhesive can be applied in a number of locations, or continuously, along the length of the vein before pressure is then applied to adhere the opposing side walls of the vein together in a collapsed configuration.

Agents that can act to retard polymerisation/curing rates are known in the art. Examples include halogenated oils, such as iodinated and brominated oils, e.g. Ethiodol, Lipiodol and Panthopaque.

When reference is made to the use of the medically acceptable adhesive 'together with' another product, the medically acceptable adhesive may be mixed together with that product prior to introduction into the vein, or alternatively the adhesive and that product may be introduced simultaneously or sequentially.

One or more sclerosing solution (such as sodium tetradecyl sulfate (STS), polidocanol, monoethanolamine oleate, and/or chromated glycerine) could possibly be used in addition to the medically acceptable adhesive, e.g. cyanoacrylate. In this situation, the ratio of medically acceptable adhesive used, e.g. cyanoacrylate, to sclerosing solution used is preferably 1:1 or more, such as 2:1 or more, e.g. 3:1 or more, for example from 4:1 to 10:1. The medically acceptable adhesive and sclerosing solution may suitably be applied separately although it is conceivable that they could also be applied together or mixed before use.

The amount of medically acceptable adhesive, e.g. cyanoacrylate, introduced can be selected based on the length of the vein from its distal end to its proximal end. However, it may be 10 ml or less, such as 8 ml or less, for example from 0.25 to 7 milliliters (ml), such as from 0.5 to 6 ml. Amounts of 5 ml or less, for example from 0.5 to 5 ml, could be considered.

Preferably, however, the amount of medically acceptable adhesive, e.g. cyanoacrylate, is 1 ml or less, for example from 0.1 to 1.0 ml, such as from 0.2 to 1.0 ml, e.g. from 0.3 to 0.9 ml. It is notable that this procedure can be carried out using only small amounts of adhesive.

In one embodiment, the medically acceptable adhesive, e.g. cyanoacrylate, is only introduced at or near to the distal end of the vein and at or near to the proximal end of the vein.

In an alternative embodiment, the medically acceptable adhesive, e.g. cyanoacrylate, is introduced at a number of positions between the distal end of the vein and the proximal end of the vein. For example, the medically acceptable adhesive may be introduced at two or more, such as three or more, e.g., four or more positions between the distal end of the vein and the proximal end of the vein.

In another embodiment, the medically acceptable adhesive, e.g., cyanoacrylate, is introduced substantially continuously between the distal end of the vein and the proximal end of the vein.

Pressure may be applied to the vein manually, and/or using apparatus, such as a compression sponge or compression bandage.

Preferably, once the medically acceptable adhesive, e.g. cyanoacrylate, has been introduced, a compression sponge is placed over the vein and a compression bandage is then applied to maintain pressure over the area containing the vein (e.g., the leg).

In the present invention, the treated veins become less noticeable in a shorter period of time, and the patient has a faster recovery time with improved results.

This invention further reduces the amount of time that patient has to wear support hosiery and decreases the number of treatment sessions for the patient, thereby reducing the cost of the treatment.

The invention also provides, in a further aspect, a kit for the treatment of undesired varicose, reticular or spider vein in a venous system of a patient, the kit comprising a medically acceptable adhesive; cannula; and catheter. Optionally, a guide wire may be included; this is particularly relevant for the treatment of large unwanted veins.

The adhesive, cannula, guide wire and catheter may be as described above.

Most preferably, the kit further comprises an inflatable cuff or a tourniquet. The inflatable cuff or tourniquet may be as described above.

In particular the cuff may include a non-inflatable section for location over the undesired vein; in a preferred embodiment the non-inflatable section of the cuff is a cut-out section in the cuff which therefore allows direct access to the skin over the undesired vein. Equally, the tourniquet may include a cut out window section as described above. This is particularly relevant for the treatment of small unwanted veins.

Alternatively, the cuff or tourniquet may include a ridged section for location over the undesired vein. This is particularly relevant for the treatment of large unwanted veins.

The adhesive, e.g. cyanoacrylate, may be provided in one or more syringe. For example, it may be provided in one or more 1 ml syringe. The total amount of adhesive, e.g. cyanoacrylate, may be 10 ml or less, such as 8 ml or less, for example from 0.25 to 7 ml, such as from 0.5 to 6 ml. Amounts of 5 ml or less, for example from 0.5 to 5 ml, could be considered. However, amounts as low as 1 ml or less, for example from 0.1 to 1.0 ml, such as from 0.2 to 1.0 ml, e.g., from 0.3 to 0.9 ml, could be provided.

Of course, it will be appreciated that the kit could include more than the amount of adhesive required for a single treatment, as the kit could be used for the treatment of more than one vein or excess could be provided in case of spillage or other wastage. Therefore although it is envisaged that the treatment of a vein would only require 1 ml or less of adhesive, more than this could be present in the kit.

In one embodiment, the kit further comprises a set of instructions. The instructions may be for the method as described above.

The kit may further comprise one or more compression device. In one embodiment, the kit further comprises one or both of: a compression sponge and a compression bandage.

The kit may further comprise a retarding agent that slows the rate of curing of the adhesive, for example an agent selected from halogenated oils, such as iodinated and brominated oils, e.g. Ethiodol, Lipiodol and Panthopaque.

The invention also provides, in a further aspect, a cyanoacrylate adhesive for the treatment of an undesired varicose, reticular or spider vein in a venous system of a patient.

The cyanoacrylate may be as described above.

The amount of cyanoacrylate used in the treatment may be 10 ml or less, such as 8 ml or less, for example from 0.25 to 7 ml, such as from 0.5 to 6 ml. Amounts of 5 ml or less, for example from 0.5 to 5 ml, could be considered. However, preferably it is 1 ml or less, for example from 0.1 to 1.0 ml, such as from 0.2 to 1.0 ml, e.g. from 0.3 to 0.9 ml.

Preferably, the undesired varicose, reticular or spider vein is in the patient's leg. In one embodiment, the vein is in the leg and below the knee.

Preferably, the cyanoacrylate adhesive is for the treatment of an undesired varicose, reticular or spider vein that is substantially emptied of blood.

Preferably, the cyanoacrylate adhesive is for the treatment of an undesired varicose, reticular or spider vein that is substantially emptied of blood, by applying pressure to the vein to cause the opposing side walls of the vein to be adhered together in a collapsed configuration by the cyanoacrylate.

Suitably the cyanoacrylate adhesive is used in combination with a retarding agent that slows the rate of curing of the adhesive, for example an agent selected from halogenated oils, such as iodinated and brominated oils, e.g. Ethiodol, Lipiodol and Panthopaque.

The invention also provides, in a further aspect, the use of a cyanoacrylate adhesive in the manufacture of a medicament for the treatment of an undesired varicose, reticular or spider vein in a venous system of a patient.

The cyanoacrylate may be as described above.

The amount of cyanoacrylate used in the medicament may be 10 ml or less, such as 8 ml or less, for example from 0.25 to 7 ml, such as from 0.5 to 6 ml. Amounts of 5 ml or less, for example from 0.5 to 5 ml, could be considered. However, preferably it is 1 ml or less, for example from 0.1 to 1.0 ml, such as from 0.2 to 1.0 ml, e.g. from 0.3 to 0.9 ml.

Preferably, the medicament is for the treatment of an undesired varicose, reticular or spider vein in the patient's leg. In one embodiment, the vein is in the leg and below the knee.

Preferably, the medicament is for the treatment of an undesired varicose, reticular or spider vein that is substantially emptied of blood.

Preferably, the medicament is for the treatment of an undesired varicose, reticular or spider vein that is substantially emptied of blood, by applying pressure to the vein to cause the opposing side walls of the vein to be adhered together in a collapsed configuration by the cyanoacrylate.

Suitably the cyanoacrylate adhesive is used in combination with a retarding agent that slows the rate of curing of the adhesive, for example an agent selected from halogenated oils, such as iodinated and brominated oils, e.g. Ethiodol, Lipiodol and Panthopaque.

The invention, together with further attendant advantages, will best be understood by reference to the following detailed description of the presently preferred embodiments of the invention, taken in conjunction with the accompanying drawings. The drawings have not been drawn to scale. It is to be understood that both the foregoing general description and the following detailed description are exemplary and explanatory and are intended to provide further explanation of the invention as claimed.

DETAILED DESCRIPTION

Figure 1:
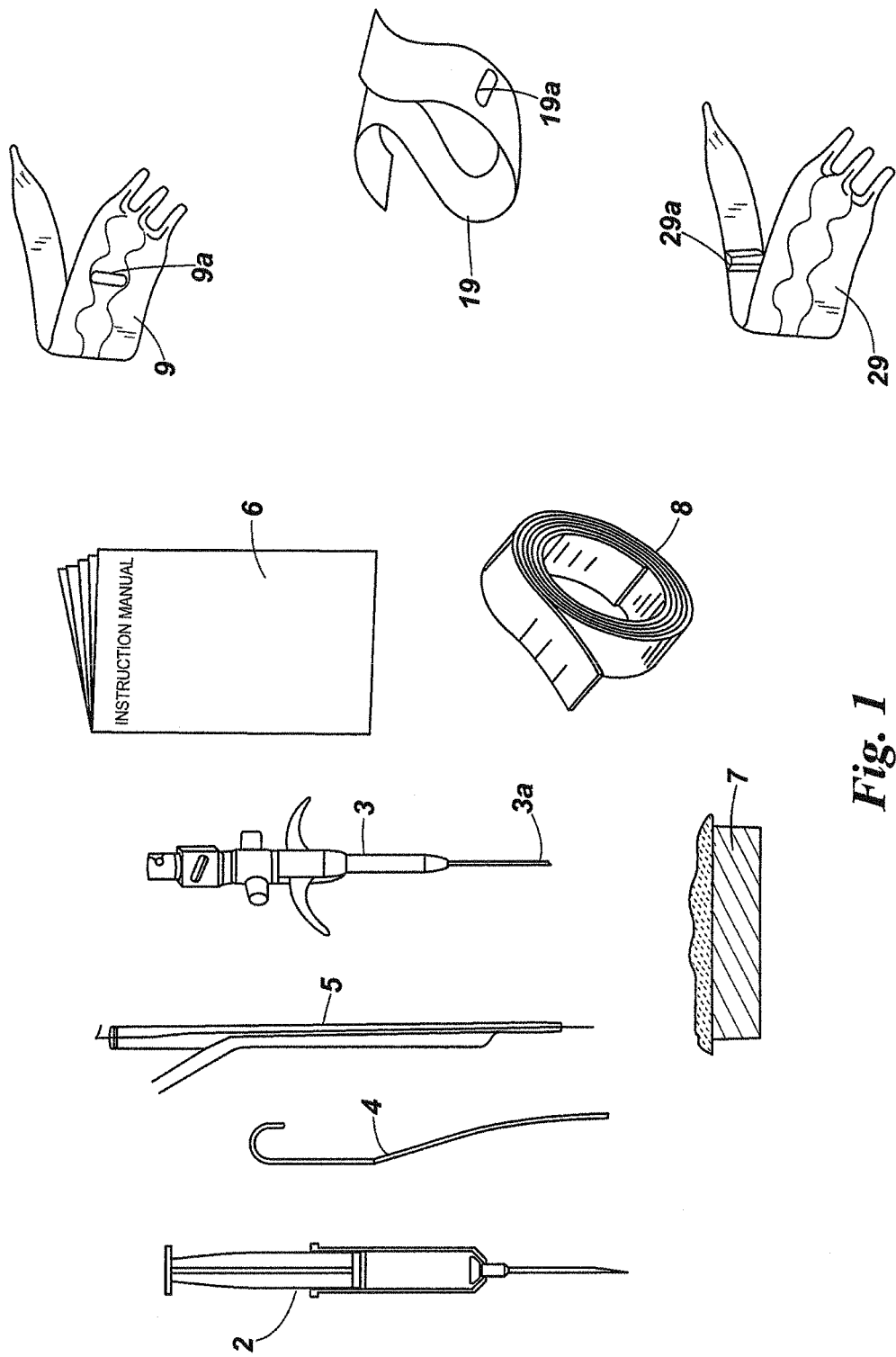
FIG. 1 is a diagrammatical view of a kit for the treatment of unwanted veins.

Before explaining the preferred embodiment in detail, it should be noted that the invention is not limited in its application or use to the details of construction and arrangement of parts illustrated in the accompanying drawings and description, because the illustrative embodiment of the invention may be implemented or incorporated in other embodiments, variations and modifications, and may be practiced or carried out in various ways. Furthermore, unless otherwise indicated, the terms and expressions employed herein have been chosen for the purpose of describing the preferred embodiment of the present invention for the convenience of the reader and are not for the purpose of limitation.

Referring now to the drawings in detail, and particularly to FIGS. 1 and 2, a surgical procedure for treating varicose or spider veins of a patient will now be described. Although the procedure will be described in reference to a vein in a patient's leg, it will be recognized that the following procedure can be used to treat a varicose or spider vein in any other part of a patient's body. The items shown in FIG. 1 are not intended to be drawn to scale relative to one another.

Figure 2:
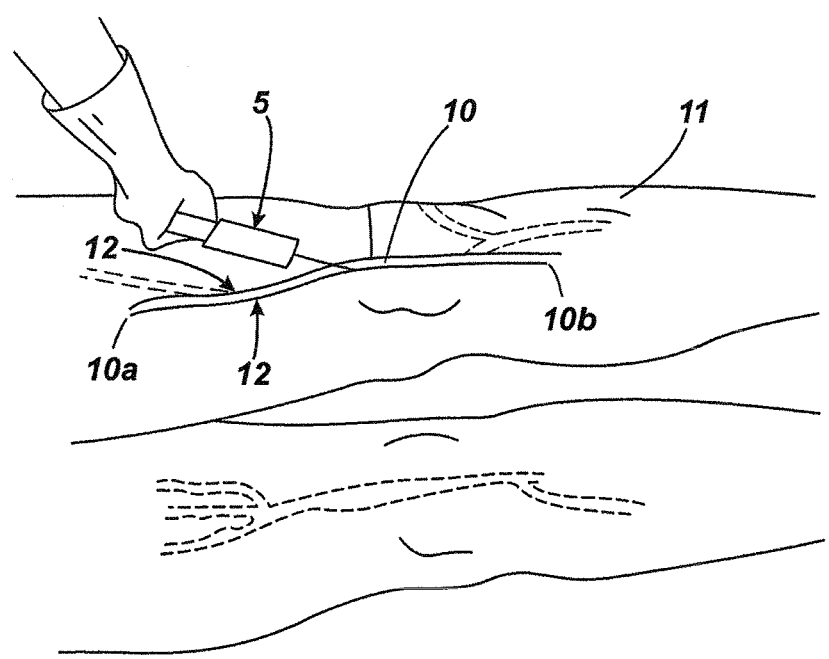
FIG. 2 is a diagrammatical view of a portion of an undesired vein in the legs of a patient being injected with a cyanoacrylate.

In the present invention, a kit of surgical apparatus for the treatment of undesired varicose or spider vein in a venous system of a patient is provided and is shown in FIG. 1. The kit comprises a number of 1 ml syringes 2 (containing adhesive), a cannula 3, an optional guide wire 4, a catheter 5, a set of instructions 6, a compression sponge 7, a compression bandage 8 and an inflatable cuff 9. Also shown are two alternatives to the inflatable cuff 9, which are a tourniquet 19 and an alternative inflatable cuff 29.

There may, for example, be one, two, three, four or five 1 ml syringes.

The cannula 3 is an intravenous cannula, which is a 22- or 24-gauge cannula and is provided with an inbuilt trocar 3a.

The guide wire 4 is flexible and has a J shaped tip. The guide wire has a length of about 20 cm.

The catheter 5 has a length of about 10 cm and is of 18-20 gauge. The catheter is made of a flexible plastics material, such as polyurethane, polypropylene, polyethylene, or poly vinyl chloride. The catheter has a distal lumen to run over the guide wire 4.

The inflatable cuff 9 is securable around a limb, e.g. around an adult lower leg, using Velcro® hook and loop releasable fastenings. The inflatable cuff 9 includes a non-inflatable section which is a cut-out section 9a. This is shaped and sized to allow direct access to the skin over the undesired vein.

In an alternative embodiment the alternative inflatable cuff 29 may be used. This does not have a cut-out section but includes a ridged section 29a for location over the undesired vein, for applying additional pressure to exsanguinate the vein. The ridged section is suitably trapezoidal in shape but may be other shapes such as a triangular prism.

In another alternative embodiment the tourniquet 19 may be used. This is securable around a limb, e.g. around an adult lower leg, and can be tightened to apply pressure thereto. The tourniquet 19 includes a cut-out window section 19a. This is shaped and sized to allow direct access to the skin over the undesired vein.

The adhesive may be any adhesive that has adhesive properties and is sufficiently non toxic that it can be used in the human body, such as a cyanoacrylate. In this embodiment, the adhesive is methyl 2-cyanoacrylate, n-butyl-2-cyanoacrylate, i-butyl-2-cyanoacrylate, or 2-octyl cyanoacrylate.

The methods of the invention will be described with reference to FIG. 2, where an unwanted varicose vein 10 in a patient's leg 11 is shown. The vein has opposing side walls 12 and extends from a proximal end 10a to a distal end 10b. However, although a varicose vein is shown, it will be appreciated that the methods also can be used for reticular and spider veins as appropriate.

Method 1—Large Unwanted Vein

The cannula 3 is introduced into the unwanted vein. In this regard, the trocar 3a is used to puncture the vein and then the cannula cannulates the vein.

The catheter 5 is then introduced into the vein using a Seldinger wire technique.

Accordingly, the guide wire 4 is introduced into the cannula 3 that has cannulated the vein and is threaded along the vein. In this regard, the guide wire is threaded along the maximum length of vein that can be navigated. The guide wire may be threaded along the vein under direct vision of the unwanted vein. Alternatively, an imaging tool, e.g., ultrasound, can be used to visualise the unwanted vein.

The catheter 5 is then passed over the guide wire 4 to ensure correct location of the catheter in the vein. The guide wire is then withdrawn.

The inflatable cuff 29 with the ridged section is placed over the leg, with the ridged section being located over the unwanted varicose vein 10.

The blood vessels in the vicinity of the undesired vein are emptied of blood by inflating the inflatable cuff to apply pressure sufficient to exsanguinate.

The undesired vein 10 is also substantially emptied of blood, by applying pressure using the ridged section 29a of the cuff. The ridge assists in applying additional pressure to force all blood out of the undesired vein.

After the vein has been substantially emptied of blood, pressure may then applied to both the proximal end 10a and distal end 10b of the vein in order to prevent the vein re-filling with blood.

The catheter 5 may be slowly withdrawn from the distal end of the vein towards the proximal end of the vein, with cyanoacrylate adhesive being introduced into the vein from the distal end of the catheter as the catheter is withdrawn. The cyanoacrylate is therefore introduced at a number of positions between the distal end of the vein and the proximal end of the vein. Specifically, the cyanoacrylate is introduced substantially continuously between the distal end of the vein and the proximal end of the vein.

Method 2—Small Unwanted Vein

The inflatable cuff 9 is placed over the leg, with the cut out section 9a being located over the unwanted varicose vein 10.

The trocar 3a of the cannula 3 is used to puncture the vein at one end, accessing the vein through the exposed skin within the cut out section of the cuff.

The catheter 5 is then inserted into that end of the vein.

The blood vessels in the vicinity of the undesired vein are emptied of blood by inflating the inflatable cuff 9 to apply pressure sufficient to exsanguinate.

The undesired vein 10 is also substantially emptied of blood, e.g. by applying pressure manually to the unwanted vein.

After the vein has been substantially emptied of blood, pressure may then applied to both the proximal end 10a and distal end 10b of the vein in order to prevent the vein re-filling with blood. A tourniquet may be used to maintain pressure in this regard.

The catheter is then used to inject the cyanoacrylate at the end of the vein, and manual is pressure applied to the outside of the vein to push the acrylate along the length of the vein.

In this method the tourniquet 19 could be used instead of the cuff 9, with the tourniquet simply being tightened to apply sufficient pressure in place of the step of inflating the cuff.

In either of the two methods, once the cyanoacrylate has been introduced, pressure is applied to the vein to cause the opposing side walls 12 of the vein 10 to be adhered together in a collapsed configuration by the cyanoacrylate adhesive. In this regard, the compression sponge 7 is placed over the vein and the compression bandage 8 is then applied to maintain pressure over the patient's leg.

In either of the two methods, prior to the step of introducing the adhesive, the vein may be flushed with glucose solution.

Although the present invention has been described in detail by way of illustration and example, it should be understood that a wide range of changes and modifications can be made to the preferred embodiments described above without departing in any way from the scope and spirit of the invention.

Thus, the described embodiments are to be considered in all respects only as illustrative and not restrictive, and the scope of the invention is, therefore, indicated by the appended claims rather than the foregoing description. All changes that come within the meaning and range of equivalency of the claims are to be embraced within their scope.

The invention claimed is:

1. A method of treating an undesired varicose, reticular or spider vein in a venous system of a patient, the undesired vein having opposing side walls and extending from a proximal end to a distal end, the method comprising the steps of:
    substantially emptying the vein of blood between its proximal end and distal end;
    introducing a medically acceptable adhesive into the substantially emptied vein; and
    applying pressure to the vein to cause the opposing side walls of the vein to be adhered together in a collapsed configuration by the adhesive,
    wherein the method further comprises a step of:
    substantially emptying of blood at least one blood vessel that connects with the undesired vein, prior to the step of introducing the adhesive, such that when the adhesive is introduced the adhesive does not enter into blood vessels that surround said at least one blood vessel that connects with the undesired vein, as there is no blood flow to allow the adhesive to enter into these blood vessels, and
    wherein in this step blood is emptied from said at least one blood vessel that connects with the undesired vein by compression, using either:
    (i) an inflatable cuff which is placed over the part of the body containing the at least one blood vessel that connects with the undesired vein and is inflated to apply pressure to said at least one blood vessel, in order to expel blood from the at least one blood vessel, wherein the inflatable cuff includes a non inflatable section which is a cut-out section that is shaped and sized to allow direct access to a section of skin located over the undesired vein, or
    (ii) a tourniquet that is placed over the part of the body containing the at least one blood vessel connecting with the undesired vein and is used to apply pressure to said least one blood vessel, in order to expel blood from the at least one blood vessel, wherein the tourniquet includes a cut-out window section that is shaped and sized to allow direct access to a section of skin located over the undesired vein,
    with the cut-out section of the inflatable cuff or the cut-out window section of the tourniquet being sized so as to be locatable over the undesired vein while substantially not covering any major blood vessels connecting with or in the vicinity of the undesired vein, such that the inflatable cuff or tourniquet allows blood to be expelled from said at least one blood vessel connecting with the undesired vein without restricting access to the undesired vein.

2. The method of claim 1, wherein the medically acceptable adhesive is introduced into the vein using a catheter.

3. The method of claim 1, wherein the medically acceptable adhesive is a cyanoacrylate adhesive.

4. The method of claim 1, wherein blood is emptied from blood vessels connecting with the undesired vein prior to the step of substantially emptying the undesired vein of blood.

5. The method of claim 1, wherein blood is emptied from blood vessels connecting with the undesired vein after the step of substantially emptying the undesired vein of blood.

6. The method of claim 1, wherein the cut-out section of the inflatable cuff or the cut-out window section of the tourniquet is from 2 cm to 10 cm in length and from 1 cm to 3 cm in width.

7. The method of claim 1, wherein the medically acceptable adhesive introduced is in an amount of 5 ml or less.

8. The method of claim 7, wherein the medically acceptable adhesive is used in an amount from 0.1 to 1.0 ml.

* * * * *